United States Patent
Hsu et al.

(10) Patent No.: US 10,493,430 B2
(45) Date of Patent: Dec. 3, 2019

(54) METHOD FOR FABRICATING A TITANIUM-CONTAINING SILICON OXIDE MATERIAL WITH HIGH THERMAL STABILITY AND APPLICATIONS OF THE SAME

(71) Applicant: ORIENTAL UNION CHEMICAL CORP., Kaohsiung (TW)

(72) Inventors: Yu-Chuan Hsu, Kaohsiung (TW); Hsi-Chin Tsai, Kaohsiung (TW)

(73) Assignee: Oriental Union Chemical Corp., Kaohsiung (TW)

( * ) Notice: Subject to any disclaimer, the term of this patent is extended or adjusted under 35 U.S.C. 154(b) by 0 days.

(21) Appl. No.: 16/127,839

(22) Filed: Sep. 11, 2018

(65) Prior Publication Data
US 2019/0015817 A1    Jan. 17, 2019

Related U.S. Application Data

(63) Continuation-in-part of application No. 15/474,718, filed on Mar. 30, 2017, now abandoned.

(30) Foreign Application Priority Data

Nov. 28, 2016 (TW) .............................. 105139094 A (51) Int. Cl.
*B01J 23/00* (2006.01)
*C07D 301/19* (2006.01)
(Continued)

(52) U.S. Cl.
CPC ......... *B01J 21/063* (2013.01); *B01J 29/0308* (2013.01); *B01J 29/89* (2013.01);
(Continued)

(58) Field of Classification Search
CPC ....... C07D 301/19; B01J 21/063; B01J 21/08; B01J 37/082; B01J 37/04; B01J 37/009
(Continued)

(56) References Cited

U.S. PATENT DOCUMENTS 3,923,843 A * 12/1975 Wulff .................. B01J 21/063
                                                549/529
4,833,260 A *  5/1989 Neri .................... B01J 29/035
                                                549/531
(Continued)

FOREIGN PATENT DOCUMENTS

CN           104556104      *  4/2015

OTHER PUBLICATIONS

C. T. Kresge et al., "Ordered mesoporous molecular sieves synthesized by a liquid-crystal template mechanism", Nature, vol. 359, Oct. 22, 1992, pp. 710-712.
(Continued)

Primary Examiner — Taylor V Oh
(74) Attorney, Agent, or Firm — Muncy, Geissler, Olds & Lowe, P.C.

(57) ABSTRACT

The present invention discloses a method for fabricating a titanium-containing silicon oxide material with high thermal stability and applications of the same, wherein a titanium source, a silicon source, an alkaline source, a template molecule and a peroxide are formulated into an aqueous solution; the aqueous solution reacts to generate a solid product; the solid product is separated from the aqueous solution with a solid-liquid separation process and dried; the solid product is calcined to obtain a titanium-containing silicon oxide material with high specific surface area. The titanium-containing silicon oxide material fabricated by the present invention has high thermal stability. Therefore, it still possesses superior catalytic activity after calcination.
(Continued)

The titanium-containing silicon oxide material can be used to catalyze epoxidation of olefin and is very useful in epoxide production.

22 Claims, 2 Drawing Sheets

(51) Int. Cl.

| | | |
|---|---|---|
| *B01J 21/06* | (2006.01) | |
| *B01J 35/10* | (2006.01) | |
| *B01J 37/04* | (2006.01) | |
| *B01J 37/08* | (2006.01) | |
| *C01B 33/20* | (2006.01) | |
| *B01J 37/00* | (2006.01) | |
| *B01J 29/89* | (2006.01) | |
| *B01J 29/03* | (2006.01) | |

(52) U.S. Cl.
CPC ....... *B01J 35/1038* (2013.01); *B01J 35/1061* (2013.01); *B01J 37/0018* (2013.01); *B01J 37/04* (2013.01); *B01J 37/08* (2013.01); *C01B 33/20* (2013.01); *C07D 301/19* (2013.01); *B01J 35/1057* (2013.01); *B01J 2229/186* (2013.01); *B01J 2229/32* (2013.01); *C01P 2002/74* (2013.01); *C01P 2006/14* (2013.01); *C01P 2006/16* (2013.01); *C01P 2006/37* (2013.01)

(58) Field of Classification Search
USPC .......................................... 549/529; 502/350
See application file for complete search history.

(56) References Cited

U.S. PATENT DOCUMENTS

| | | |
|---|---|---|
| 5,143,879 A | 9/1992 | Whitehurst |
| 6,512,128 B2 | 1/2003 | Yamamoto et al. |
| 6,887,823 B2 | 5/2005 | Yamamoto et al. |
| 7,018,950 B2 | 3/2006 | Yamamoto |
| 2007/0260074 A1* | 11/2007 | Buijink ................. B01J 21/063 549/529 |

OTHER PUBLICATIONS

S. Hitz et al., "Influence of Template Extraction on Structure, Activity, and Stability of MCM-41Catalysts", Journal of Catalysis. vol. 168, 1997, pp. 194-206.

Peter T. Tanev et al., "Titanium-containing mesoporous molecular sieves for catalytic oxidation of aromatic compounds", Nature, vol. 368, Mar. 24, 1994, pp. 321-323.

Kaifeng Lin et al., "Formation of better catalytically active titanium species in Ti-MCM-41 by vapor-phase silylation", Journal of Catalysis, vol. 235, 2005, pp. 423-427.

Kaifeng Lin et al., "Synthesis and catalytic activity of Ti-MCM-41 nanoparticles with highly active titanium sites", Journal of Catalysis, vol. 254, 2008, pp. 64-70.

Kaifeng Lin et al., "Direct room-temperature synthesis of methyl-functionalized Ti-MCM-41 nanoparticles and their catalytic performance in epoxidation", Journal of Catalysis, vol. 263, 2009, pp. 75-82.

* cited by examiner

METHOD FOR FABRICATING A TITANIUM-CONTAINING SILICON OXIDE MATERIAL WITH HIGH THERMAL STABILITY AND APPLICATIONS OF THE SAME

CROSS REFERENCE TO RELATED APPLICATION

This application is a Continuation-in-Part of co-pending application Ser. No. 15/474,718, filed on Mar. 30, 2017, for which priority is claimed under 35 U.S.C. § 120; and this application claims priority of Application No. 105139094 filed in Taiwan on Nov. 28, 2016 under 35 U.S.C. § 119;

BACKGROUND OF THE INVENTION

Field of the Invention

The present invention relates to a method for fabricating a titanium-containing silicon oxide material with high thermal stability and applications of the same, particularly to a titanium-containing silicon oxide material with high thermal stability, which is synthesized by a template-based method, wherein a calcination process is used to remove the template molecules and make the material have a high specific surface area. The titanium-containing silicon oxide material is used as a catalyst to directly oxidize olefin into an epoxide.

Description of the Related Art

Titanium-containing silicon oxide materials normally have porous structure with large surface area, able to function as a superior absorptive agent, a catalyst or a catalyst carrier. In 1992, there has been a paper publishing a template-based method for fabricating a silicon dioxide material (Please refer to the periodical Nature, vol. 359 (1992), p. 710). The abovementioned method uses a calcination process to remove the organic template and make the silicon dioxide material have a higher specific surface area and a catalytic activity. In addition to the calcination process, the organic template can also be removed with an extraction process (Please refer to the periodical J. Catal. vol. 168 (1997), p. 194, and the U.S. Pat. No. 5,143,879).

In the template-based method for fabricating titanium-containing silicon oxide material, titanium is introduced into a silicon dioxide material having high surface area to diversify the catalytic activity of the material. However, titanium is sensitive to temperature. If the titanium-containing silicon oxide is fabricated with the template-based method and calcined to remove the organic template, the catalytic activity of the material will be degraded (Please refer to the periodical Nature vol. 368 (1994), p. 321; J. Catal. vol. 235 (2005), p. 423; J. Catal. vol. 254 (2008), p. 64; J. Catal. vol. 263 (2009), p. 75). In order to keep out of the intrinsic temperature sensitivity of titanium, the organic template of the titanium-containing silicon oxide fabricated with the template-based method should be removed with an extraction method lest the superior catalytic activity be degraded (Please refer to U.S. Pat. Nos. 7,018,950, 6,887,823, and 6,512,128).

However, in comparison with the extraction method, the calcination method to remove the organic template has many advantages, including less organic residual material, higher mechanical strength, higher hydrothermal stability, less equipment, and simpler operation.

In order to overcome the abovementioned problems, the applicant of the patent particularly develops a template-based method for fabricating a titanium-containing silicon oxide material with high thermal stability and applications of the same, wherein the organic template is removed with a calcination method to make the titanium-containing silicon oxide material present a superior catalytic activity that can catalyze epoxidation of olefin to generate epoxide.

SUMMARY OF THE INVENTION

The primary objective of the present invention is to provide a method for fabricating a titanium-containing silicon oxide material with high thermal stability and applications of the same, wherein a titanium source, a silicon source, an alkaline source, a template molecule, a solvent and a peroxide are mixed to form an aqueous solution and react in the aqueous solution to generate a product, and wherein the product is filtered, dried and calcined to obtain a titanium-containing silicon oxide material, and wherein the titanium-containing silicon oxide material has high specific surface area and high thermal stability, able to catalyze epoxidation of olefin to generate epoxide.

In order to achieve the abovementioned objective, the present invention proposes a method for fabricating a titanium-containing silicon oxide material with high thermal stability, wherein a titanium source, a silicon source, an alkaline source, a template molecule, a solvent and a peroxide are mixed uniformly to form an aqueous solution. The aqueous solution is persistently agitated at a temperature of −20-200° C. for 0.5-180 hours. Then, a solid product is separated from liquid, dried and calcined to obtain a titanium-containing silicon oxide material with high thermal stability. The titanium-containing silicon oxide material with high thermal stability is expressed by Formula (I) in an anhydrous state:

$$x\text{TiO}_2(1-x)\text{SiO}_2 \qquad (I)$$

wherein x ranges from 0.00001-0.5;
wherein the titanium-containing silicon oxide material has an average pore size of 10 angstroms or more;
wherein the titanium-containing silicon oxide material has a pore size of 90% or more of the total pore volume of 5 to 200Å; and
wherein the titanium-containing silicon oxide material has a specific pore volume of 0.2 cm$^3$/g or more.

The titanium source used in the abovementioned method may be but is not limited to be a titanate, an inorganic titanium source, or a combination thereof. The silicon source may be but is not limited to be an amorphous silicon dioxide, an alkoxysilane, a silicate, or a combination thereof. The alkaline source may be any material able to increase the pH value of the system, such as an inorganic alkaline, an organic alkaline, a counter ion that is an anion containing hydroxyl groups and also an organic molecule able to function as a template, or a combination thereof. The template molecule may be but is not limited to be a cation surfactant, an anion surfactant, a non-ionic surfactant, an ampholytic surfactant, or a combination thereof. The solvent may be but is not limited to be an alcohol-group solvent, such as methyl alcohol, ethyl alcohol, n-propyl alcohol, isopropyl alcohol, vinyl butanol, allyl butanol, butyl alcohol, sec-butyl alcohol, tert-butyl alcohol, amyl alcohol, cyclohexanol, benzyl alcohol, diol, or a combination thereof. The peroxide may be but is not limited to be hydrogen peroxide or an organic peroxide. The peroxide can be directly added to the aqueous reaction solution. Alternatively, the peroxide is generated in an environment with a suitable catalytic agent or in a suitable reaction condition.

The present invention also proposes a method for fabricating an epoxide, wherein the titanium-containing silicon oxide material with high thermal stability fabricated by the present invention is used as a catalyst to catalyze the reaction of olefin and oxidant to generate epoxide.

Before used to catalyze epoxidation, the titanium-containing silicon oxide material with high thermal stability fabricated by the present invention can be silylated or impregnated with a transition metal to enhance the catalytic activity thereof.

The present invention does not strictly limit the quantity of the catalyst as long as the quantity of the catalyst is sufficient to make the epoxidation reaction fully completed in the shortest time. In the epoxidation reaction, the molar ratio of olefin to oxidant ranges from 1:100 to 100:1, preferably from 1:10 to 10:1. The present invention does not particularly limit the reaction temperature of the epoxidation reaction. The reaction temperature is normally within 0-200° C., preferably within 25-150° C. The present invention does not particularly limit the reaction pressure of the epoxidation reaction as long as the reaction pressure is greater than the pressure keeping all the reactants in a liquid state. The reaction pressure is preferably within 1-100 atm. The reaction time of the epoxidation reaction is within 1 minute-48 hours, preferably within 5 minutes-8 hours. The epoxidation reaction can be undertaken in batches, continuously, or semi-continuously in various types of reactors and instruments, such as fixed bed reactors, transport bed reactors, fluid bed reactors, slurry reactors, and continuously-stirred tank reactors.

The method of the present invention features a simple process and a low fabrication cost. The catalyst fabricated thereby presents high thermal stability and superior catalytic activity. Therefore, the present invention is very useful in industry.

Below, embodiments will be described in detail to make easily understood the objectives, technical contents, characteristics and accomplishments of the present invention.

DETAILED DESCRIPTION OF THE INVENTION

Figure 1:
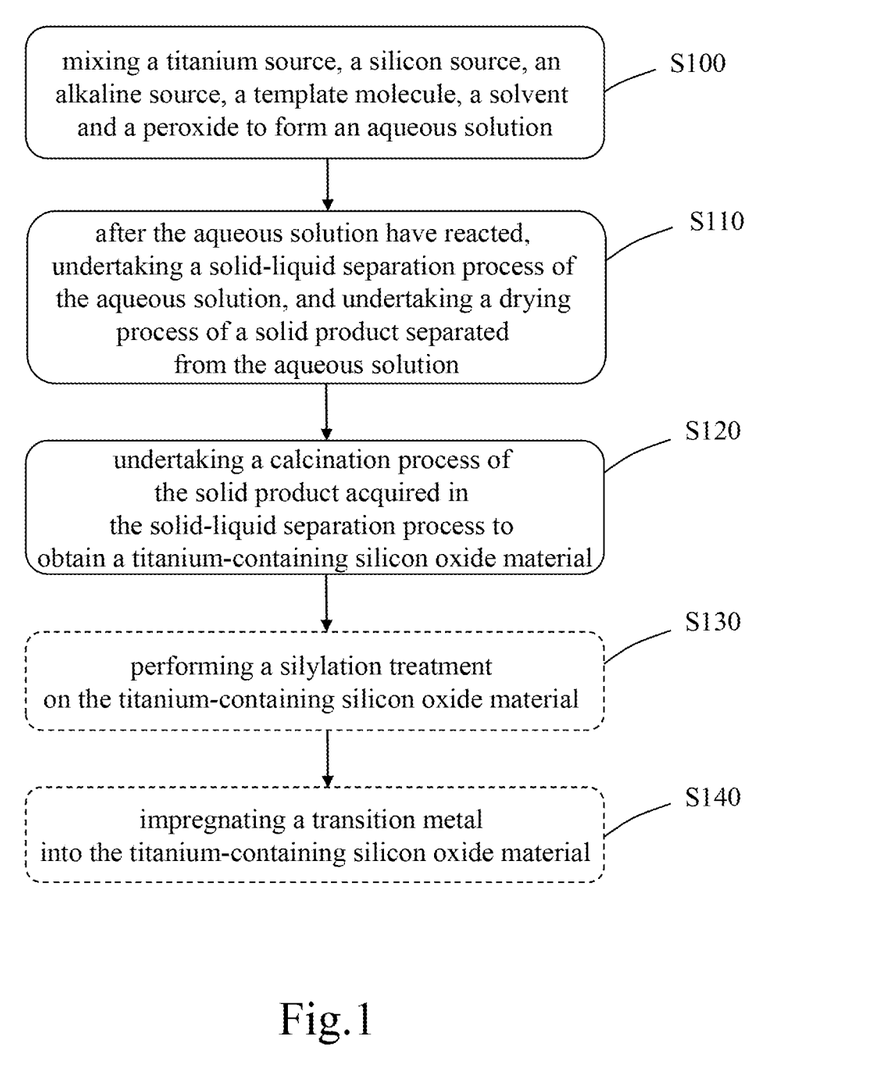
FIG. 1 shows a flowchart of a method for fabricating a titanium-containing silicon oxide material with high thermal stability according to one embodiment of the present invention.

Refer to FIG. 1. The method for fabricating a titanium-containing silicon oxide material with high thermal stability of the present invention comprises 5 steps: Steps S100-S140. Steps S100-S120 explain the method for fabricating a titanium-containing silicon oxide material with high thermal stability. Step S130 and Step S140 describe two steps that may be added to the process of fabricating a titanium-containing silicon oxide material with high thermal stability to provide the titanium-containing silicon oxide material with high catalytic activity. In practical operation, one or more of Step S130 and Step S140 may be used in a single fabrication process. However, all the abovementioned steps are jointly presented in a single flowchart for simplicity, wherein the dot-line blocks mean that the corresponding steps are optional.

In Step S100, mix a titanium source, a silicon source, an alkaline source, a template molecule, a solvent and a peroxide to form an aqueous solution, and agitate the aqueous solution uniformly.

The titanium source used in the present invention may be but is not limited to be a titanate, an inorganic titanium source, or a combination thereof. The titanate may be but is not limited to be selected from a group including tetramethyl titanate, tetraethyl titanate, tetrapropyl orthotitanate, tetraisopropyl titanate, tetrabutyl orthotitanate, tetra sec-butyl titanate, tetrabutyl isotitanate, tetra tert-butyl titanate, tetra (2-ethylhexyl) titanate, tetraoctadecyl orthotitanate, and combinations thereof. The inorganic titanium source may be a titanium halide (such as titanium trichloride, titanium tetrachloride, titanium tribromide, titanium tetrabromide, titanium triiodide, or titanium tetraiodide), titanium sulfate, titanium dioxide, or a combination thereof. The abovementioned titanium sources may be used singly or jointly.

The silicon source used in the present invention may be but is not limited to be an amorphous silicon dioxide, an alkoxysilane, a silicate, or a combination thereof. The amorphous silicon dioxide has a general formula $SiO_2$, which may be in form of a powdered silicon dioxide material or a bulk silicon dioxide material, such as smoked silica, fumed silica, silica gel, or silica sol. The alkoxysilane may be a silane containing 4 alkoxy groups, such as tetramethylorthosilicate, tetraethylorthosilicate, tetrapropylorthosilicate, or the like. Besides, the alkoxysilane containing other functional groups may be also used as the silicon sources, such as alkyltrialkoxysilanes, dialkyldialkoxysilanes, trialkylmonoalkoxysilanes, and the likes. The silicate may be water glass, potassium silicate, magnesium silicate, calcium silicate, or the like. The abovementioned silicon sources may be used singly or jointly.

The alkaline source used in the present invention may be but is not limited to be an organic alkaline, an inorganic alkaline, a counter ion that is an anion containing hydroxyl groups and also an organic molecule able to function as a template. The organic alkaline may be a nitrogen-containing material, such as ammonium hydroxide, a pyridine, an imidazole, a benzimidazole, a histidine, or the like. The inorganic alkaline may be a hydroxide containing a metal ion, such as lithium hydroxide, sodium hydroxide, potassium hydroxide, magnesium hydroxide, calcium hydroxide, strontium hydroxide, barium hydroxide, or the like. The counter ion is an anion containing hydroxyl groups and also an organic molecule able to function as a template, such as dodecyl trimethyl ammonium hydroxide, tetradecyl dimethyl benzyl ammonium hydroxide, cetyltrimethylammonium hydroxide, hexadecyl tributyl ammonium hydroxide, benz yltrimethylammonium hydroxide, dimethyldidodecylammonium hydroxide, hexadecylpyridinium, trimethyloctadecylammonium hydroxide, or the like. The abovementioned alkaline sources may be used singly or jointly.

The template molecule used in the present invention may be but is not limited to be a cation surfactant, an anion surfactant, a non-ionic surfactant, or an ampholytic surfactant. The cation surfactant is selected from a group including alkyl ammoniums, dialkyl ammoniums, trialkyl ammoniums, benzyl ammoniums, alkylpiridinium, and the likes. The anion surfactant is selected from a group including alkylsulfate ions, alkylphosphate ions and the likes. The non-ionic surfactant is selected from a group including polyalkylene oxides, block copolymers, alkylamines, and the likes. The ampholytic surfactant is selected from a group including 3-(N, N-dimethylmyristylammonio) propanesulfonate and long carbon chain molecules simultaneously having ammonium groups and carboxylic groups. The abovementioned template molecules are molecules containing nitrogen or molecules containing quaternary ammonium salts. The nitrogen-containing molecules having Formula (II) and the quaternary ammonium salt-containing molecules having Formula (III) are more suitable to function as template molecules.

$$R^1NR^2R^3 \qquad \qquad (II)$$

$$[NR^1R^4R^5R^6]^+ \qquad \qquad (III)$$

In Formula (II), $R^1$ is a functional group containing a straight hydrocarbon chain or a branch hydrocarbon chain; each of the straight hydrocarbon chain and the branch hydrocarbon chain has 2-36 carbon atoms; each of $R^2$ and $R^3$ is a hydrogen atom, an alkyl group, or a phenyl group; each of the alkyl group has 1-8 carbon atoms, and each of the phenyl group has 6-8 carbon atoms. In Formula (III), $R^1$ is a functional group containing a straight hydrocarbon chain or a branch hydrocarbon chain; each of the straight hydrocarbon chain and the branch hydrocarbon chain has 2-36 carbon atoms; each of $R^4$-$R^6$ is an alkyl group or a phenyl group; each of the alkyl group has 1-8 carbon atoms, and each of the phenyl group has 6-8 carbon atoms.

As mentioned above, in Formula (II), $R^1$ is a functional group in form of a straight hydrocarbon chain or a branch hydrocarbon chain, which has 2-36 carbon atoms. However, it is preferred that the straight hydrocarbon chain or the branch hydrocarbon chain of $R^1$ has 10-18 carbon atoms. As mentioned above, in Formula (II), each of $R^2$ and $R^3$ is a hydrogen atom, an alkyl group, or a phenyl group, and each of the alkyl group has 1-8 carbon atoms, and each of the phenyl group has 6-8 carbon atoms. However, it is preferred that each of $R^2$ and $R^3$ is a hydrogen atom. In detail, the nitrogen-containing molecules, which function as template molecules and are expressed by Formula (II), include dodecylamine, n-tetradecylamine, hexadecylamine, octadecylamine, tetradecyl dimethyl amine, hexadecylmethylamine, hexadecyldimethylamine, and the likes.

As mentioned above, in Formula (III), $R^1$ is a functional group in form of a straight hydrocarbon chain or a branch hydrocarbon chain, which has 2-36 carbon atoms. However, it is preferred that the straight hydrocarbon chain or the branch hydrocarbon chain of $R^1$ has 10-18 carbon atoms. As mentioned above, in Formula (III), each of $R^4$-$R^6$ is an alkyl group having 1-8 carbon atoms, or a phenyl group having 6-8 carbon atoms. However, it is preferred that the alkyl group is a methyl group. In detail, the nitrogen-containing cations, which function as template molecules and are expressed by Formula (III), include dodecyl trimethyl ammonium, tetradecyl dimethyl benzyl ammonium, cetyltrimethylammonium, hexadecyl tributyl ammonium, benzyltrimethylammonium, dimethyldidodecylammonium, hexadecylpyridinium, trimethyloctadecylammonium, and the likes. The abovementioned template molecules may be used singly or jointly.

The solvent used in the present invention may be but is not limited to be an alcohol-group solvent. In detail, the alcohol-group solvent is referred to an alcohol having 1-10 carbon atoms, such as methyl alcohol, ethyl alcohol, n-propyl alcohol, isopropyl alcohol, vinyl butanol, allyl butanol, butyl alcohol, sec-butyl alcohol, tert-butyl alcohol, amyl alcohol, cyclohexanol, benzyl alcohol, diol, or a combination thereof.

The peroxide used in the present invention may be but is not limited to be hydrogen peroxide or an organic peroxide. Hydrogen peroxide has a general formula: H—O—O—H. The organic peroxide has a general formula: R—O—O—H, wherein R denotes an acyl group or a hydrocarbon group, which has 1-20 carbon atoms (preferably 1-10 carbon atoms), and which has or has not substitute groups. The R group is selected from a group including acyl groups, alkyl groups, cycloalkyl groups, secondary or tertiary alkyl groups, hydrocarbon groups, cycloalkenyl groups, aralkyl groups, and aralkenyl groups. In detail, the organic peroxide may be but is not limited to be peroxyformic acid, peroxyacetic acid, peroxypropionic acid, peroxystearic acid, peroxypalmitic acid, peroxylauric acid, meta-chloroperoxybenzoic acid, ethylbenzene hydroperoxide, cumene hydroperoxide, tertiary butyl hydroperoxide, or cyclohexyl hydroperoxide, tetralin hydroperoxide, methyl ethyl ketone peroxide, methylcyclohexene hydroperoxide, or the like. The abovementioned peroxides may be used singly or jointly.

In the present invention, the peroxide can be directly added to the formulated aqueous solution. Alternatively, the peroxide is generated in an environment with a suitable catalytic agent or in a suitable reaction condition. For example, the peroxide can be generated in a reaction of barium oxide and dilute sulfuric acid, a hydrolysis reaction of ammonium persulfate, a catalytic reaction of hydrogen and oxygen in a metal catalyst, a catalytic reaction of aldehyde, alkyl, or aromatic alkyl in air or oxygen with or without a catalytic agent.

In the present invention, the molar ratio of titanium sources to silicon sources in the aqueous solution is 0.00001-1, preferably 0.00008-0.5. The molar ratio of template molecules to the sum of titanium sources and silicon sources is 0.01-2. The molar ratio of alkaline sources to template molecules is 0.1-6, preferably 1-4. The molar ratio of template molecules to water is 0.001-1, preferably 0.005-0.5. The weight ratio of solvents to water is 0-5, preferably 0.001-3. The molar ratio of peroxide to the sum of titanium sources and silicon sources is 0.001-5, preferably 0.01-3.

Next, in Step S110, place the aqueous solution at a temperature of −20-200° C., and persistently agitate the aqueous solution for 0.5-180 hours. Next, separate the solid product from the reaction solution with an appropriate solid liquid separation method. Then, dry the solid product in an oven at a temperature of 30-120° C. for 0.5-6 hours.

Next, in Step S120, calcine the dried solid product at a temperature of 300-800° C., preferably 350-650° C., for 1-9 hours, preferably 3-6 hours. Thereby is obtained a titanium-containing silicon oxide material with high thermal stability and with high specific surface area, which can be expressed by Formula (I) in an anhydrous state:

$$xTiO_2(1-x)SiO_2 \qquad \qquad (I)$$

wherein x ranges from 0.00001 to 0.5;
wherein the titanium-containing silicon oxide material has an average pore size of 10 angstroms or more;
wherein the titanium-containing silicon oxide material has a pore size of 90% or more of the total pore volume of 5 to 200 Å; and
wherein the titanium-containing silicon oxide material has a specific pore volume of 0.2 cm$^3$/g or more.

The titanium-containing silicon oxide material of the present invention preferably has at least one peak showing an interplanar spacing (d) of larger than 18 Å, or no peak showing an interplanar spacing (d) in a X-ray diffraction (XRD). The peak showing an interplanar spacing (d) as herein referred to means a peak derived from the crystallinity and regularity of a solid, and a broad peak derived from an amorphous part may exist. When, a peak showing an interplanar spacing (d) of larger than 18 Å exists in a X-ray diffraction, it is preferable that this peak is a part of a peak group showing the structure of a hexagonal system.

The titanium-containing silicon oxide material of the present invention preferably has an absorption peak in the range of 960±5 cm$^{-1}$ in the infrared absorption spectrum. This peak is considered to correspond to titanium introduced into a silica skeleton.

In the present invention, a titanium source, a silicon source, and a template molecule are formulated into an aqueous solution to obtain a titanium-containing silicon oxide material after reactions, which related to a templating method. The titanium source and the silicon source are combined by co-condensation reaction. Also, during combining reaction, the aqueous solution reacts to generate a solid product with holes. The Ti is distributed on the surface of the Silicon dioxide and into the framework.

Moreover, the templating agent, such as cetyltrimethylammonium bromide (CTAB), of the present invention does not necessary need to have high molecular symmetry. Additionally, the hydrothermal treatment is not necessary. Therefore, the manufacturing costs are reduced.

The titanium-containing silicon oxide material fabricated by the present invention can be used as a catalyst. Before used to catalyze a reaction, the titanium-containing silicon oxide material may be processed with a silylation treatment to decrease the intrinsic acidity, modify the surface characteristic and enhance the catalytic activity.

The silylation treatment can be realized with a vapor-based method using a vapor-phase silylation agent to react with the titanium-containing silicon oxide material, or a liquid-based method using a liquid-phase silylation agent to react with the titanium-containing silicon oxide material. The silylation treatment can be undertaken in an ordinary way with one or more types of organic silanes.

The organic silane used to realize silylation may be but is not limited to be selected from a group including halogenosilanes (having a general formula $R^1R^2R^3SiX$), silazanes (having a general formula $[R^4R^5R^6Si]_2NH$), methylsilane-imidazoles (having a general formula $R^7R^8R^9Si[N_2C_3H_3]$) and methylsilane-amines (having a general formula $(R^{10})_3SiN(R^{11})_2$), wherein $R^1$, $R^2$ and $R^3$ are identical or different, and each of $R^1$, $R^2$, and $R^3$ is a saturated alkyl group having 1-6 carbon atoms or a saturated phenyl group having 6 carbon atoms, and wherein $R^4$, $R^5$ and $R^6$ are identical or different, and each of $R^4$, $R^5$ and $R^6$ is an alkyl group having 1-6 carbon atoms, a haloalkyl group having 1-6 carbon atoms, or a phenyl group having 6 carbon atoms, and wherein each of $R^7$-$R^{11}$ is a saturated alkyl group having 1-3 carbon atoms. The preferred organic silane is selected from a group including hexamethyldisilazane, silylamines, trimethylsilyl chloride, n-(trimethylsilyl)-imidazol, and combinations thereof. The solvent used in silylation may be but is not limited to be selected from a group including aromatic hydrocarbon compounds having 6-16 carbon atoms, saturated alkanes having 6-16 carbon atoms, and combinations thereof. The preferred solvent is selected from a group including toluene, benzene, cyclohexane, isopropylbenzene, and combinations thereof. In silylation, the weight ratio of the organic silane to the titanium-containing silicon oxide material is 0.01-1, preferably 0.1-0.8; the weight ratio of the solvent to the titanium-containing silicon oxide material is 1-200, preferably 1-100. The reaction temperature of silylation is 25-200° C., preferably 50-150° C. The reaction time of silylation is 0.5-3 hours, preferably 1-2 hours.

Step S140 is an optional procedure. In Step S140, incorporate a transition metal into the titanium-containing silicon oxide material to enhance the catalytic activity.

Dependent on requirement, a transition metal may be incorporated into the titanium-containing silicon oxide material with an impregnation method, a precipitation method, a blending method, or another like method. In the impregnation method, a solution of a transition metal is dispersed in an appropriate solvent to form a mixture solution, and the mixture solution is further mixed with the titanium-containing silicon oxide material to form a titanium-containing silicon oxide material impregnated with the transition metal. Dependent on requirement, the titanium-containing silicon oxide material impregnated with the transition metal may be further dried and calcined. The concentration of the transition metal in the titanium-containing silicon oxide material is 0.01-10 wt %, preferably 0.005-5 wt %. The transition metal is inside or outside the framework of the titanium-containing silicon oxide material.

The titanium-containing silicon oxide material fabricated by the present invention can be granulated in any stage, e.g. before calcination, after calcination, before silylation, after silylation, etc. Dependent on requirement, granulation can be undertaken with an appropriate method, such a compression molding method or an extrusion molding method, to make the titanium-containing silicon oxide material have a special range of particle diameters.

Because of having high specific surface area and highly dispersed positions of active titanium, the titanium-containing silicon oxide material fabricated by the present invention can function as a catalyst to catalyze oxidation and selective oxidation of many organic compounds. Besides, if a third group of components, such as aluminum, is added to the titanium-containing silicon oxide material of the present invention to increase the acidity, the titanium-containing silicon oxide material may catalyze alkylation reactions and reforming reactions.

Figure 2:
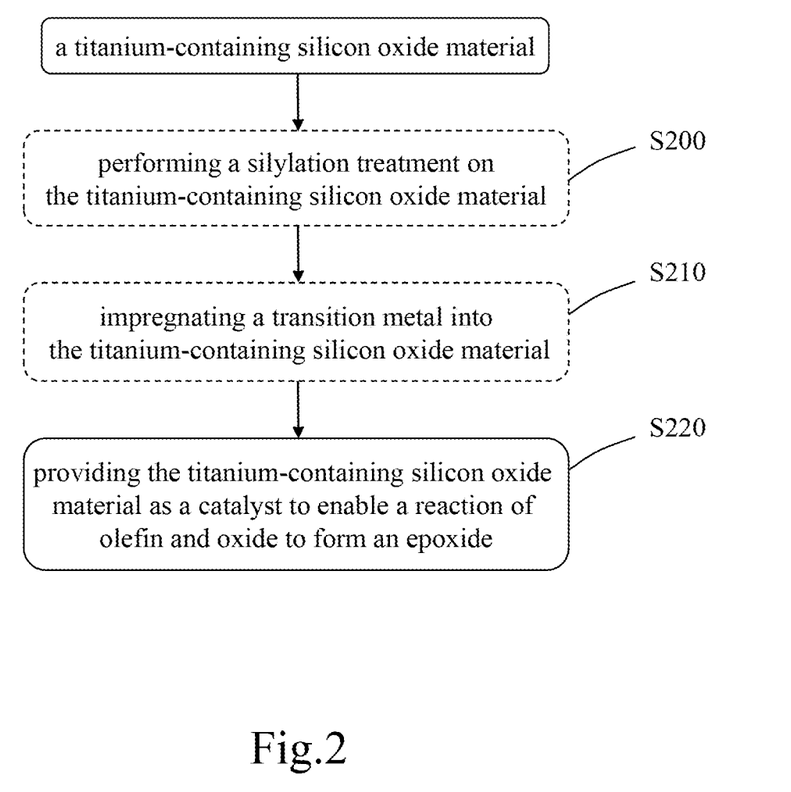
FIG. 2 shows a flowchart of a method for fabricating an epoxide according to one embodiment of the present invention.

Refer to FIG. 2 a flowchart demonstrating the steps of applying the titanium-containing silicon oxide material fabricated by the present invention to fabricate an epoxide compound. The flowchart includes 3 steps: Steps S200-S220. Step S220 describes a method for fabricating an epoxide. Step S200 and Step S210 respectively steps that can be optionally added to the epoxide fabrication process to enhance the catalytic activity. In practical operation, one or more of Step S200 and Step S210 may be added to a single fabrication process. For simplicity, these steps are presented on FIG. 2 jointly, and the dotted line blocks indicate that the corresponding steps are optional.

As shown in Step S200 and Step S210, before the catalytic reaction, the catalytic activity of the catalyst can be enhanced via undertaking silylation and/or transition metal impregnation to the titanium-containing silicon oxide material. The technical details of Step S200 and Step S210 are the same as Step S130 and Step S140, and will not repeat herein. Besides, Step S200 and Step S210 can also collaborate with the granulation process.

In Step S220, use the titanium-containing silicon oxide material as the catalyst to catalyze the epoxidation reaction of olefin and oxide to form an epoxide.

The titanium-containing silicon oxide material used in the epoxidation reaction may be in form of powder, agglomerates, micro-spheres, or a single block. The titanium-containing silicon oxide material can be shaped via squeezing, compressing, or another appropriate method. The olefin-group compound used in the epoxidation reaction may be but is not limited to be selected from a group including aliphatic compounds, and cyclic compounds (further including monocyclic compounds, bicyclic compounds and polycyclic compounds). Further, the olefin-group compound used in the epoxidation reaction may be but is not limited to be selected from a group including mono-olefin compounds, di-olefin compounds, and poly-olefin compounds. While the quantity of the double bonds of the olefin-group compound is greater than 2, the double bonds may be conjugated double bonds or non-conjugated double bonds. The mono-olefin compounds may be but is not limited to be the olefin-group compounds having 2-60 carbon atoms and allowed to have a substitute group, preferably a relatively-stable substitute group. The mono-olefin compounds may be but is not limited to be selected from a group including ethylene, propylene, 1-butene, isobutene, 1-hexene, 2-hexene, 3-hexene, 1-octene, 1-decene, styrene, and cyclohexene. The di-olefin compounds may be but is not limited to be butadiene or isoprene.

The oxidant used in the epoxidation reaction may be but is not limited to be an organic peroxide having a general formula: R—O—O—H, wherein R denotes an alkyl radical having 3-20 carbon atoms (preferably 3-10 carbon atoms). The alkyl radical may be but is not limited be a secondary alkyl group, a tertiary alkyl group, or an aralkyl group, such as the tertiary butyl group, the tertiary pentyl group, the cyclopentane group, or the 2-phenyl-2-propyl group. The organic peroxide may be but is not limited to be ethylbenzene hydroperoxide, cumene hydroperoxide, tertiary butyl hydroperoxide, or cyclohexyl hydroperoxide. While cumene hydroperoxide is used as the organic peroxide, the product of the reaction is alpha-Cumyl alcohol. Alpha-Cumyl alcohol can be converted into alpha-methyl styrene via dehydration. In addition to many applications in the industry, alpha-methyl styrene can be hydrogenated into cumene, which is the precursor of cumene hydroperoxide. The other organic peroxides also have the similar characteristic.

The oxidant used in the epoxidation reaction may also be hydrogen peroxide having a general formula: H—O—O—H. Hydrogen peroxide may be in form of an aqueous solution and reacts with olefin to generate epoxide and water.

The oxidant functioning as a reactant may be a concentrated/diluted pure/impure material.

In one embodiment, a solvent or diluent is added to the epoxidation reaction to make the reaction undertake in a liquid state. The solvent or diluent is in a liquid state in the environment of the epoxidation reaction and inert to all the reactants and products. The abovementioned solvent may be but is not limited to be methyl alcohol, acetone, ethyl benzene, ethylbenzene, cumene, isobutene, cyclohexene, or a combination thereof. The abovementioned solvent may be a material existing in the solution of the oxidant to be used in the reaction. For example, while the solution of cumene hydroperoxide is used as the oxidant, the cumene is used as raw material for oxidant. At the same time, cumene can function as the solvent for the solution of oxidant and reaction, and addition of another solvent is unnecessary in such a case.

In the abovementioned method, the present invention does not strictly limit the quantity of the catalyst as long as the quantity of the catalyst is sufficient to make the epoxidation reaction fully completed in the shortest time. In the epoxidation reaction, the molar ratio of olefin to oxidant ranges from 1:100 to 100:1, preferably from 1:10 to 10:1. The present invention does not particularly limit the reaction temperature of the epoxidation reaction. The reaction temperature is normally within 0-200° C., preferably within 25-150° C. The present invention does not particularly limit the reaction pressure of the epoxidation reaction as long as the reaction pressure is greater than the pressure keeping all the reactants in a liquid state. The reaction pressure is preferably within 1-100 atm. The reaction time of the epoxidation reaction is the shortest time able to obtain the highest yield of the epoxide product. The reaction time of the epoxidation reaction generally is within 1 minute-48 hours, preferably within 5 minutes-8 hours. The epoxidation reaction can be undertaken in batches, continuously, or semi-continuously in various types of reactors and instruments, such as fixed bed reactors, transport bed reactors, fluid bed reactors, slurry reactors, and continuously-stirred tank reactors.

Below, embodiments are used to demonstrate how the present invention fabricates a titanium-containing silicon oxide material with high thermal stability and uses the material as a catalyst to catalyze the epoxidation reaction of olefin and oxidant and generate an epoxide.

Embodiment I

Fabrication of a Titanium-containing Silicon Oxide Material:

Use 0.58 kg of tetraisopropylorthotitanate, 15.6 kg of tetraethylorthosilicate, 4.56 kg of 28 wt % ammonia aqueous solution, 7.81 kg of cetyltrimethylammonium hydroxide, 2.42 kg of 35 wt % hydrogen peroxide aqueous solution, 3 kg of isopropyl alcohol, and 24.6 kg of water to prepare a reaction liquid. Agitate the reaction liquid at an ambient temperature for 3 hours. Filter the reaction liquid to remove the solution and obtain a powder. Dry the powder at a temperature of 70° C. Heat the dried powder at a temperature rising speed of 5° C./min to a temperature of 550° C., and calcine the dried powder at the temperature of 550° C. for 6 hours. Then, let the powder cool down naturally.

Fabrication of Propylene Epoxide:

Use 7.5 g of titanium-containing silicon oxide material fabricated in Embodiment I as the catalyst. Uniformly mix the catalytic material, 225 g of 25 wt % cumene hydroperoxide solution (cumene is the solvent), and 125 g of propylene in a 1-liter airtight autoclave, and undertake a reaction at a temperature of 85° C. for less than 1.5 hours. The result of the reaction is shown in Table.1.

Embodiment II

Fabrication of a Titanium-containing Silicon Oxide Material:

The process for fabricating a titanium-containing silicon oxide material is the same as Embodiment I except Embodiment II further takes 16.5 g of the titanium-containing silicon oxide material to undertake silylation. Mix the titanium-containing silicon oxide material with 165 g of toluene and 11.2 g of hexamethyldisilazane uniformly to form a solution. Next, agitate the solution at a temperature of 120° C. for 1 hour to obtain a suspension. Next, filter the suspension to obtain a powder as the catalytic material.

Fabrication of Propylene Epoxide:

The process for fabricating propylene epoxide is the same as Embodiment I except the titanium-containing silicon oxide material fabricated in Embodiment II is used as the catalyst. The result of the reaction is shown in Table. 1.

Embodiment III

Fabrication of a Titanium-containing Silicon Oxide Material:

The process for fabricating a titanium-containing silicon oxide material is the same as Embodiment II except Embodiment III further uses a compression molding method to granulate the titanium-containing silicon oxide material having a particle diameter of 1-2 mm.

Fabrication of Propylene Epoxide:

The process for fabricating propylene epoxide is the same as Embodiment I except the titanium-containing silicon oxide material fabricated in Embodiment III is used as the catalyst. The result of the reaction is shown in Table.1.

Embodiment IV

Fabrication of a Titanium-containing Silicon Oxide Material:

The process for fabricating a titanium-containing silicon oxide material is the same as Embodiment III.

Fabrication of Propylene Epoxide:

Take the titanium-containing silicon oxide material fabricated in Embodiment IV as the catalyst, and fill the catalyst into a fixed bed reactor having an inner diameter of 2 inch and a length of 75 cm. Mix 25 wt % cumene hydroperoxide solution (cumene is the solvent) and propylene in a static mixer to form a mixture, continuously feed the mixture into the fixed bed rector through the bottom side of the reactor, wherein the molar ration of propylene to cumene hydroperoxide is 8, and the WHSV of 25 wt % cumene hydroperoxide solution is 10 $h^{-1}$. The system is maintained at a temperature of 85° C. and a pressure of 30 bar to make the epoxidation reaction of propylene persistently take place in the catalytic layer. The reaction liquid is discharged from the top side of the reactor and passed through a gas-liquid separation tank. After the excess propylene is separated, the products are analyzed. The result of the reaction is shown in Table.1.

Comparison I

Fabrication of a Titanium-containing Silicon Oxide Material:

Fabricate a titanium-containing silicon oxide material according to J. Catal. vol. 254 (2008), p. 64. Take 16.5 g of the titanium-containing silicon oxide material to undertake a silylation reaction. Mix the titanium-containing silicon oxide material with 165 g toluene and 11.2 g hexamethyldisilazane uniformly to form a solution, and agitate the solution at a temperature of 120° C. for 1 hour to obtain a suspension. Next, filter the suspension to obtain a powder and dry the powder.

Fabrication of Propylene Epoxide:

The process for fabricating propylene epoxide is the same as Embodiment I except the titanium-containing silicon oxide material fabricated in Comparison I is used as the catalyst. The result of the reaction is shown in Table.1.

Comparison II

Use 0.72 kg of tetra isopropyl orthotitanate, 20.3 kg of tetra ethyl orthosilicate, 2.7 kg of 28 wt % ammonia aqueous solution, 0.05 kg of potassium hydroxide, 7.81 kg of cetyltrimethylammonium hydroxide, 3.9 kg of isopropyl alcohol, and 38.3 kg of water to prepare a reaction liquid. Agitate the reaction liquid at an ambient temperature for 3 hours. Filter the reaction liquid to remove the solution and obtain a powder. Dry the powder at a temperature of 70° C. Heat the dried powder at a temperature rising speed of 5° C./min to a temperature of 550° C., and calcine the dried powder at the temperature of 550° C. for 6 hours. Then, let the powder cool down naturally.

Take 16.5 g of the titanium-containing silicon oxide material to undertake silylation reaction. Mix the titanium-containing silicon oxide material with 165 g toluene and 11.2 g hexamethyldisilazane uniformly to form a solution, and agitate the solution at a temperature of 120° C. for 1 hour to obtain a suspension. Next, filter the suspension to obtain a powder and dry the powder.

Fabrication of Propylene Epoxide:

The process for fabricating propylene epoxide is the same as Embodiment I except the titanium-containing silicon oxide material fabricated in Comparison II is used as the catalyst. The result of the reaction is shown in Table.1.

TABLE 1

|  | E1 (Note 3) | E2 | E3 | E4 | C1 (Note 4) | C2 |
|---|---|---|---|---|---|---|
| Conversion rate of cumene hydroperoxide (%) (Note 1) | 79.9 | 99.4 | 98.1 | 99 | 27 | 50 |
| Selection rate of propylene epoxide (%) (Note 2) | 75.4 | 97.1 | 96.9 | 97 | 94 | 96 |

(Note 1):
conversion rate of cumene hydroperoxide = consumed quantity of cumene hydroperoxide/added quantity of cumene hydroperoxide × 100%.
(Note 2):
selection rate of propylene epoxide = generated quantity of propylene epoxide/consumed quantity of cumene hydroperoxide × 100%.
(Note 3):
E denotes an embodiment.
(Note 4):
C denotes a comparison.

Table.1 indicates the following facts: Embodiment I proves that the calcined titanium-containing silicon oxide material of the present invention show distinguished catalytic activity in catalyzing the epoxidation reaction of olefin; Embodiment II the silylation of the calcined titanium-containing silicon oxide material of the present invention can obviously increase the catalytic activity in catalyzing the epoxidation reaction of olefin; Embodiment III proves that the granulation of the titanium-containing silicon oxide material of the present invention does not affect the catalytic activity thereof; Embodiment IV proves that after a long-time and continuous epoxidation reaction of olefin, the titanium-containing silicon oxide material of the present invention still keeps its superior catalytic activity; Comparisons I and II prove that the catalytic activity of the titanium-containing silicon oxide material of the present invention in the epoxidation reaction of olefin is much higher than the catalytic activity of the titanium-containing silicon oxide material fabricated with the conventional technologies.

In summary, the present invention proposes a method for fabricating a titanium-containing silicon oxide material with high thermal stability, which can uses a common and simple template-based method to fabricate a titanium-containing silicon oxide material with high thermal stability. The titanium-containing silicon oxide material fabricated by the present invention has high catalytic activity, able to function as a catalyst to successfully catalyze the epoxidation reaction of olefin. No matter whether in a batch reactor or in a continuous reactor, the titanium-containing silicon oxide material fabricated by the present invention always presents superior and stable catalytic activity. The present invention also proposes applications of the titanium-containing silicon oxide material fabricated by the present invention.

The present invention has been demonstrated with the abovementioned embodiments. However, it should be understood: these embodiments are only to exemplify the present invention but not to limit the scope of the present invention. Therefore, any equivalent modification or variation according to the spirit or characteristics of the present invention is to be also included within the scope of the present invention.

What is claimed is:

1. A method for fabricating a titanium-containing silicon oxide material with high thermal stability, comprising steps:
mixing a titanium source, a silicon source, an alkaline source, a template molecule, a solvent and a peroxide to form an aqueous solution;
enabling a co-condensation reaction of said aqueous solution without using a hydrothermal treatment, undertaking a solid-liquid separation process of said aqueous solution, and undertaking a drying process of a solid product separated from said aqueous solution; and
undertaking a calcination process of said solid product acquired in said solid-liquid separation process to obtain a titanium-containing silicon oxide material having Formula (I) in an anhydrous state:

$$x TiO_2 (1-x) SiO_2 \qquad (I)$$

wherein x ranges from 0.00001-0.5;
wherein said titanium-containing silicon oxide material has an average pore size of 10 angstroms or more;
wherein said titanium-containing silicon oxide material has a pore size of 90% or more of the total pore volume of 5 to 200 Å; and
wherein said titanium-containing silicon oxide material has a specific pore volume of 0.2 cm$^3$/g or more;
wherein said template molecule is a nitrogen-containing molecule having a formula: $R^1NR^2R^3$ or a quaternary ammonium salt-containing molecule having a formula: $[NR^1R^4R^5R^6]^+$, or a combination thereof, and wherein $R^1$ is a functional group containing a straight hydrocarbon chain or a branch hydrocarbon chain; each of said straight hydrocarbon chain and said branch hydrocarbon chain has 2-36 carbon atoms; each of $R^2$ and $R^3$ is a hydrogen atom, an alkyl group, or a phenyl group; each of $R^4$-$R^6$ is an alkyl group or a phenyl group; each of said alkyl group has 1-8 carbon atoms; and each of said phenyl group has 6-8 carbon atoms;
wherein said titanium-containing silicon oxide material has at least one peak showing an interplanar spacing (d) of larger than 18Å, or no peak showing an interplanar spacing (d) in a X-ray diffraction (XRD).

2. The method for fabricating a titanium-containing silicon oxide material with high thermal stability according to claim 1, wherein said titanium source is a titanate, an inorganic titanium source, or a combination thereof; said silicon source is an amorphous silicon dioxide, an alkoxysilane, a silicate, or a combination thereof; said alkaline source is an inorganic alkaline, an organic alkaline, a counter ion that is an anion containing hydroxyl groups and also an organic molecule able to function as a template, or a combination thereof; said template molecule is a cation surfactant, an anion surfactant, a non-ionic surfactant, an ampholytic surfactant, or a combination thereof; said solvent is selected from a group consisting of methyl alcohol, ethyl alcohol, n-propyl alcohol, isopropyl alcohol, vinyl butanol, allyl butanol, butyl alcohol, sec-butyl alcohol, tert-butyl alcohol, amyl alcohol, cyclohexanol, benzyl alcohol, diols, and combinations thereof; said peroxide is hydrogen peroxide or an organic peroxide.

3. The method for fabricating a titanium-containing silicon oxide material with high thermal stability according to claim 2, wherein said titanate is selected from a group consisting of tetramethyl titanate, tetraethyl titanate, tetrapropyl orthotitanate, tetra isopropyl titanate, tetrabutyl orthotitanate, tetra sec-butyl titanate, tetrabutyl isotitanate, tetra tert-butyl titanate, tetra(2-ethylhexyl) titanate, tetraoctadecyl orthotitanate, and combinations thereof; said inorganic titanium source is selected from a group consisting of titanium trichloride, titanium tetrachloride, titanium tribromide, titanium tetrabromide, titanium triiodide, titanium tetraiodide, titanium sulfate, titanium dioxide, and combinations thereof.

4. The method for fabricating a titanium-containing silicon oxide material with high theimal stability according to claim 2, wherein said amorphous silicon dioxide is selected from a group consisting of smoked silica, fumed silica, silica gel, silica sol, and combinations thereof; said alkoxysilane is selected from a group consisting of tetramethylorthosilicate, tetraethylorthosilicate, tetrapropylorthosilicate, alkyltrialkoxysilanes, dialkyldialkoxysilanes, trialkylmonoalkoxysilanes, and combinations thereof; said silicate is selected from a group consisting of water glass, potassium silicate, magnesium silicate, calcium silicate, and combinations thereof.

5. The method for fabricating a titanium-containing silicon oxide material with high thermal stability according to claim 2, wherein said organic alkaline is selected from a group consisting of ammonium hydroxide, pyridines, imidazoles, benzimidazoles, histidines, and combinations thereof; said inorganic alkaline is selected from a group consisting of lithium hydroxide, sodium hydroxide, potassium hydroxide, magnesium hydroxide, calcium hydroxide, strontium hydroxide, barium hydroxide, and combinations thereof; said counter ion is an anion containing hydroxyl groups and also an organic molecule able to function as a template, selected from a group consisting of dodecyl trimethyl ammonium hydroxide, tetradecyl dimethyl benzyl ammonium hydroxide, cetyltrimethylammonium hydroxide, hexadecyl tributyl ammonium hydroxide, benzyltrimethylammonium hydroxide, dimethyldidodecylammonium hydroxide, hexadecylpyridinium, trimethyloctadecylammonium hydroxide, and combinations thereof.

6. The method for fabricating a titanium-containing silicon oxide material with high thermal stability according to claim 1, wherein said template molecule is selected from a group consisting of dodecylamine, n-tetradecylamine, hexadecylamine, octadecylamine, tetradecyl dimethyl amine, hexadecylmethylamine, hexadecyldimethylamine, dodecyl trimethyl ammonium, tetradecyl dimethyl benzyl ammonium, cetyltrimethylammonium, hexadecyl tributyl ammonium, benzyltrimethylammonium, dimethyldidodecylammonium, hexadecylpyridinium, trimethyloctadecylammonium, and combinations thereof.

7. The method for fabricating a titanium-containing silicon oxide material with high thermal stability according to claim 2, wherein said organic peroxide has a formula: R—O—O—H, wherein R denotes an acyl group or a hydrocarbon group, which has 1-20 carbon atoms.

8. The method for fabricating a titanium-containing silicon oxide material with high thermal stability according to claim 7, wherein said R group has 1-10 carbon atoms.

9. The method for fabricating a titanium-containing silicon oxide material with high thermal stability according to claim 7, wherein said R group is selected from a group consisting of acyl groups, alkyl groups, cycloalkyl groups, secondary or tertiary alkyl groups, hydrocarbon groups, cycloalkenyl groups, aralkyl groups, and aralkenyl groups.

10. The method for fabricating a titanium-containing silicon oxide material with high thermal stability according to claim 7, wherein said organic peroxide is selected from a group consisting of peroxyformic acid, peroxyacetic acid, peroxypropionic acid, peroxystearic acid, peroxypalmitic acid, peroxylauric acid, meta-chloroperoxybenzoic acid, ethylbenzene hydroperoxide, cumene hydroperoxide, tertiary butyl hydroperoxide, or cyclohexyl hydroperoxide, tetralin hydroperoxide, methyl ethyl ketone peroxide, methylcyclohexene hydroperoxide, and combinations thereof.

11. The method for fabricating a titanium-containing silicon oxide material with high thermal stability according to claim 1, wherein said peroxide is generated in a reaction of barium oxide and dilute sulfuric acid, a hydrolysis reaction of ammonium persulfate, a catalytic reaction of hydrogen and oxygen in a metal catalyst, a catalytic reaction of aldehyde, alkyl, or aromatic alkyl in air or oxygen with or without a catalytic agent.

12. The method for fabricating a titanium-containing silicon oxide material with high thermal stability according to claim 1, wherein a molar ratio of titanium to silicon in said aqueous solution is 0.00001-1; a molar ratio of said template molecule to a sum of titanium and silicon is 0.01-2; a weight ratio of said solvent to water is 0-5; a molar ratio of said peroxide to a sum of titanium and silicon is 0.001-5; a molar ratio of said template molecule to water is 0.001-1; a molar ratio of said alkaline source to said template molecule is 0.1-6.

13. The method for fabricating a titanium-containing silicon oxide material with high thermal stability according to claim 12, wherein a molar ratio of titanium to silicon in said aqueous solution is 0.00008-0.5; a weight ratio of said solvent to water is 0.01-3; a molar ratio of said peroxide to a sum of titanium and silicon is 0.01-3; a molar ratio of said template molecule to water is 0.005-0.5; a molar ratio of said alkaline source to said template molecule is 1-4.

14. The method for fabricating a titanium-containing silicon oxide material with high thermal stability according to claim 1, wherein said aqueous solution reacts at a temperature of −20-200° C. for 0.5-180 hours, and whereafter said drying process of said solid product separated from said aqueous solution is continuously undertaken at a temperature of 30-120° C. for 0.5-6 hours.

15. The method for fabricating a titanium-containing silicon oxide material with high thermal stability according to claim 1, wherein said calcination process is undertaken at a temperature of 300-800° C. for 1-9 hours.

16. The method for fabricating a titanium-containing silicon oxide material with high thermal stability according to claim 15, wherein said calcination process is undertaken at a temperature of 350-650° C. for 3-6 hours.

17. The method for fabricating a titanium-containing silicon oxide material with high thermal stability according to claim 1 further comprising at least one of following steps:
performing a silylation treatment on said titanium-containing silicon oxide material at a temperature of 25-200° C. for 0.5-3 hours; and
impregnating a transition metal into said titanium-containing silicon oxide material, wherein said transition metal has a concentration of 0.01-10wt % in a total weight of said titanium-containing silicon oxide material.

18. The method for fabricating a titanium-containing silicon oxide material with high thermal stability according to claim 17, wherein said transition metal has a concentration of 0.005-5wt % in a total weight of said titanium-containing silicon oxide material.

19. A method for fabricating an epoxide, comprising a step:
providing a titanium-containing silicon oxide material with high thermal stability fabricated according to claim 1 as a catalyst to enable a reaction of olefin and oxidant to form an epoxide.

20. The method for fabricating an epoxide according to claim 19, wherein said olefin is selected from a group consisting of mono-olefin compounds, di-olefin compounds, and poly-olefin compounds; said oxidant is an organic peroxide or a hydrogen peroxide; said mono-olefin compound is selected from a group consisting of ethylene, propylene, 1-butene, isobutene, 1-hexene, 2-hexene, 3-hexene, 1-octene, 1-decene, styrene, and cyclohexene; said di-olefin compound is butadiene or isoprene; said organic peroxide is selected from a group consisting of ethylbenzene hydroperoxide, cumene hydroperoxide, tertiary butyl hydroperoxide, and cyclohexyl hydroperoxide.

21. The method for fabricating an epoxide according to claim 19, wherein a molar ratio of said olefin to said oxidant ranges from 1:100 to 100:1; said olefin and said oxidant react at a temperature of 0-200° C.; said olefin and said oxidant react at a pressure greater than a pressure keeping all reactants in a liquid state; a reaction time of said olefin and said oxidant is within 1 minute-48 hours.

22. The method for fabricating an epoxide according to claim 21, wherein a molar ratio of said olefin to said oxidant ranges from 1:10 to 10:1; said olefin and said oxidant react at a temperature of 25-150° C.; said olefin and said oxidant react at a pressure of 1-100 atm; a reaction time of said olefin and said oxidant is within 5 minute-8 hours.

* * * * *